United States Patent [19]

Vollmer et al.

[11] 4,091,012
[45] May 23, 1978

[54] PRODUCTION OF TERTIARY PHOSPHINE OXIDES

[75] Inventors: Hartfrid Vollmer, Erftstadt; Georg Elsner, Bonn-Duisdorf; Bernd Lippsmeier, Hurth; Klaus Hestermann, Erftstadt, all of Germany

[73] Assignee: Hoechst Aktiengesellschaft, Frankfurt am Main, Germany

[21] Appl. No.: 780,989

[22] Filed: Mar. 24, 1977

[30] Foreign Application Priority Data

Mar. 30, 1976 Germany .............................. 2613546

[51] Int. Cl.² .......................................... C07C 120/00
[52] U.S. Cl. ................................. 260/465.1; 260/464; 260/465 R; 260/465 H; 260/465.8 R
[58] Field of Search ..................... 260/465.8 R, 465.1, 260/464, 465 H

[56] References Cited

U.S. PATENT DOCUMENTS

| | | | |
|---|---|---|---|
| 2,822,376 | 2/1958 | Hechenbleikner et al. | 260/465.1 |
| 3,145,234 | 8/1964 | Buckler et al. | 260/465.1 X |
| 3,148,206 | 9/1964 | Rauhut et al. | 260/465.8 R |

*Primary Examiner*—Joseph Paul Brust
*Attorney, Agent, or Firm*—Connolly and Hutz

[57] ABSTRACT

Production of tertiary phosphine oxides which contain nitrile groups and correspond to the following general formula I:

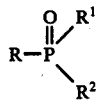

in which $R^1$ and $R_2$ each stand for a straight or branched, identical or different alkyl, cycloalkyl, aryl, alkylaryl or aralkyl group having 1 to 18 carbon atoms, and in which $R^1$ or $R_2$ may be identical with R, which stands for a radical of the following general formula II:

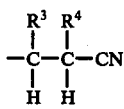

in which $R^3$ and $R^4$ each stand for a straight or branched, identical or different alkyl, cycloalkyl, aryl, alkylaryl or aralkyl group having 1 to 18 carbon atoms, and/or hydrogen atoms. The tertiary phosphine oxides are made by reacting a phosphine of the following general formula III:

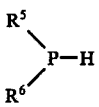

in which $R^5$ has the same meaning as $R^3$ and $R^6$ has the same meaning as $R^4$ but is no hydrogen, with an α,β-unsaturated nitrile of the following general formula IV:

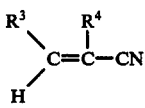

in which $R^3$ and $R^4$ have the meanings given above. The reaction is effected in a single stage in the presence of water or a water-solvent mixture and the above formula I compounds are separated from the reaction product.

7 Claims, No Drawings

PRODUCTION OF TERTIARY PHOSPHINE OXIDES

The present invention relates to a process for making tertiary phosphine oxides which contain nitrile groups and correspond to the following general formula I

   I in which $R^1$ and $R^2$ each stand for a straight or branched, identical or different alkyl, cycloalkyl, aryl, alkylaryl or aralkyl group having from 1 to 18, preferably 1 to 6, more preferably 1 to 2, carbon atoms, and in which $R^1$ or $R^2$ may be identical with R which stands for a radical of the following general formula II

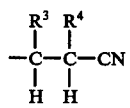   II in which $R^3$ and $R^4$ each stand for a straight or branched, identical or different alkyl, cycloalkyl, aryl, alkylaryl or aralkyl group having from 1 to 18, preferably 1 to 6, carbon atoms and/or a hydrogen atom.

It has already been described that phosphines containing β-cyanoethyl groups can be alkylated by means of alkyl halides to give quaternary phosphonium halides which can be split with the use of alcoholates and converted to other asymmetric phosphines.

As disclosed in U.S. Pat. Nos. 3,005,013 and 3,116,317, tris-(2-cyanoethyl)-phosphine can be reacted with methyl iodide to give a phosphonium iodide which can be treated with basic sodium ethylate and split into bis-(2-cyanoethyl)-methylphosphine which is obtained in a yield of about 60% (cf. M. Brayson, P. T. Keough, G. A. Johnson; J. Am. Chem. Soc. 81, 4806 (1959)).

$$(NC-CH_2CH_2)_3P + CH_3I \rightarrow$$
$$[(NC-CH_2CH_2)_3{}^{\oplus}PCH_3]$$
$$I[(NC-CH_2CH_2)_3{}^{\oplus}PCH_3] I + NaOC_2H_5 \rightarrow$$
$$CH_3P(CH_2CH_2CN)_2 + C_2H_5OCH_2CH_2CN + NaI$$

Bis-(2-cyanoethyl)-methylphosphine is also obtainable (cf. S. L. Kommissarova, R. K. Valetdinov and E. V. Kuznetsov, Zh, obshch. Khim 41, 322-24 (1971)) by reacting bis-(hydroxymethyl)-methylphosphine with acrylonitrile.

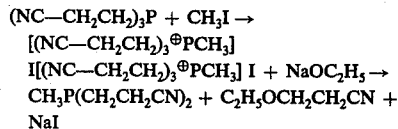

The above reaction is carried out at temperatures of −15° to −20° C and the resulting reaction product is worked up at temperatures not higher than 25° C so as to substantially avoid polymerization of the acrylonitrile.

The cyanoethylphosphines obtainable by the process just described can be oxidized with $H_2O_2$ of 30% strength and converted to the corresponding phosphine oxides (E. V. Kuznetsov, I. V. Sorokina and R. K. Valetdinov Zh. Obshch Khim 33, 2631-2634 (1963)).

It has also been described that 2-cyanoethyl-alkylchlorophosphines can be reacted with α,β-unsaturated carboxylic acid amides. This reaction which is accompanied by a dehydrochlorination reaction yields phosphine oxides containing two cyanoalkyl groups. The reaction takes the course shown in the following equation:

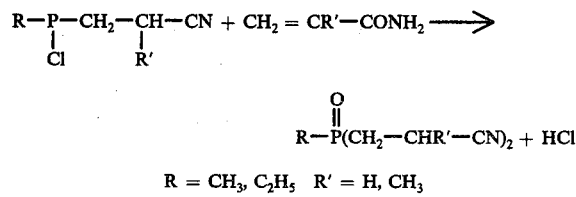

R = $CH_3$, $C_2H_5$  R' = H, $CH_3$ (cf. V. K. Khairullin, G. V. Dimitrieva, I. A. Aleksandrova and M. A. Vasyanina, Izv. Akad. Nauk USSR, Ser. Khim 12, 2744-2749 (1973)).

(I. A. Aleksandrova, L. I. Ufimtsova, U. K. Khairullin and G. V. Dimitrieva, Zh. Obshch Khim. 44, 2125-2129 (1974)).

It is also known that tertiary phosphines which contain at least one hydroxymethyl group can be subjected to a rearrangement reaction and thereby converted to methyl phosphine oxides. The rearrangement reaction is effected at elevated temperature with the addition of catalysts, such as $CCl_4$, Lewis acids, radical-yielding agents or under ultraviolet light. The two other substituents of the phosphine subjected to the rearrangement reaction may have, e.g. cyano-groups linked thereto, which remain unaffected during the rearrangement reaction (cf. German patent specifications "Offenlegungsschriften" Nos. 2,407,460, 2,413,823, 2,413,824, 2,356,257 and 2,357,276).

The processes described heretofore for making tertiary phosphine oxides containing nitrile groups are highly unsatisfactory inasmuch as they present a plurality of disadvantages in respect of the following points: The yield of desirable pure product is as low as about 60% and a plurality of reaction steps is necessary for synthesizing the desirable compound. In addition to this, the above prior processes call for the use of starting material which is difficult to produce at least commercially. In other words, the processes described heretofore use starting material which is not readily available and expensive so that they are substantially not suitable for use on an industrial scale. Needless to say therefore it is highly desirable to have a process wherein commercially readily available starting material is subjected to a simple reaction yielding the desired products.

In accordance with the present invention we now unexpectedly provide a novel process for making tertiary phosphine oxides which contain nitrile groups and correspond to the above general formula I, which comprises: reacting a phosphine of the following general formula III:

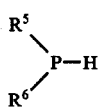   III in which $R^5$ has the same meaning as $R^3$ and $R^6$ has the same meaning as $R^4$ but is no hydrogen, with an α,β-unsaturated nitrile of the following general formula IV:

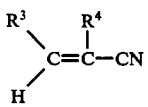

in which $R^3$ and $R^4$ have the meanings given above, the reaction being effected in a single stage in the presence of water or a water-solvent mixture; and separating the above formula I compounds from the reaction product.

A highly unexpected result of the present process resides in the fact that the above formula I compounds are obtained in a simple reaction involving a single reaction stage without any need to isolate the tertiary phosphine intermediate product and to separately oxidize the tertiary phosphine intermediate to tertiary phosphine oxide.

A further unexpected result resides in the fact that the reaction is substantially free from side reactions, e.g., polymerization, of the formula IV $\alpha,\beta$-unsaturated nitriles.

It is good practice to effect the reaction in contact with a catalyst. The useful catalysts primarily comprise chlorides, sulfates or acetates of metals, such as cadmium, nickel, manganese and cobalt, which may be used in combination with aqueous ammonia or an aqueous solution of an alkali metal or alkaline earth metal hydroxide. The metal salt may conveniently be used in proportions of 0.1 to 10 millimol, preferably 1 to 5 millimol, based on the starting material. The aqueous solution of the base may contain ammonia or the alkali metal or alkaline earth metal hydroxide in proportions of 0.01 to 0.2 mol, preferably 0.05 to 0.15 mol, based on the starting material.

The reaction should be effected at a temperature between 0° and 50° C, preferably 15° and 25° C.

The reaction mixture may be admixed with water and, if desired, with further solvents which primarily comprise alcohols and acetonitrile. It is also preferable to effect the reaction under inert gas, e.g., nitrogen.

The quantitative ratio of the reaction components which does not materially affect the reaction may be varied within wide limits. It is preferable, however, to use the formula III and formula IV reactants in the stoichiometric ratio necessary for the formation of the formula I compounds.

It is also preferable in accordance with this invention to place the formula IV $\alpha,\beta$-unsaturated nitrile together with a catalyst in an aqueous phase, e.g., water or a solvent-water mixture, to add the formula III phosphine at the rate necessary to maintain the reaction temperature between 15° and 25° C, and by removing the solvent to separate the resulting formula I tertiary phosphine oxide from the reaction product.

The present process offers the following principal advantages: It is a simple and single stage reaction producing good yields of desirable final product without any need to separate intermediary material.

The compounds made by the present process are interesting intermediates for use in phospho-organic syntheses. It is possible, for example, to hydrogenate the nitrile groups to amino groups or saponify them to carboxylic groups.

EXAMPLE 1

108 g (2 mols) of acrylonitrile was introduced into 200 ml of a mixture of equal parts of water and acetonitrile in an agitator-provided vessel which was scavenged with nitrogen, and 1 g of $NiCl_2 \cdot 6H_2O$ in 25 ml of concentrated ammonia was added. Next, 34 g (0.7 mol) of methylphosphine which was used together with nitrogen as an inert gas was introduced into the apparatus within 2 hours. The temperature was maintained within the range 15° to 25° C by cooling from the outside. Following this, the solvent was separated by distillation. The yield was 94%, based on methylphosphine. bp $_{0.03\ mm}$:206°–210° C. The product contained 17.8 weight% of phosphorus (calculated: 18.23 weight%).
$^1$H-NMR spectrum:

| $CH_3P$ duplet | = 1.6 ppm |
|---|---|
| $-CH_2-$ } multiplet | = 2.34 ppm |
|  | = 2.77 ppm |

EXAMPLE 2

The reaction was effected as described in Example 1. The catalyst was 1 g of $MnCl_2 \cdot 4\ H_2O$.

EXAMPLE 3

The reaction was effected as described in Example 1 with 134 g (2 mols) of methylacrylonitrile. The yield was 92%, based on methylphosphine.

The final product contained 14.9 weight% of phosphorus (calculated: 15.63 weight%).

EXAMPLE 4

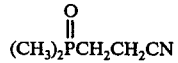

53 g (1 mol) of acrylonitrile was placed in 200 ml of a mixture of equal parts of water and acetonitrile in an agitator-provided vessel which was scavenged with nitrogen, and 0.5 ml of $NiCl_2 \cdot 6H_2O$ in 15 ml of concentrated ammonia was added. Next, 34 g (0.55 mol) of dimethylphosphine which was used in admixture with nitrogen as an inert gas was introduced within 2 hours. The temperature was maintained within the range 15° to 27° C by cooling from the outside. The solvent was removed by distillation.

The yield was 91 weight%, based on dimethylphosphine. The final product contained 23.1 weight% of phosphorus (calculated: 23.62 weight%).
$^1$H-NMR spectrum:

| $-CH_3-$duplet | = 1.86 ppm |
|---|---|
| $-CH_2-$multiplet | = 2.51 ppm. |

We claim:

1. A process for making tertiary cyanoalkylphosphine oxides corresponding to the following general formula I:

  I in which $R^1$ and $R^2$ each stand for a straight or branched, identical or different alkyl group having 1 to 6 carbon atoms, and in which $R^1$ or $R^2$ may be identical with R, which stands for a radical of the following general formula II:

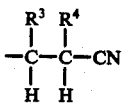  II in which $R^3$ and $R^4$ each stand for a straight or branched, identical or different alkyl group having 1 to 6 carbon atoms, or a hydrogen atom, which comprises: reacting under inert gas a phosphine of the following general formula III:

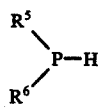  III in which $R^5$ has the same meaning as $R^3$ and $R^6$ has the same meaning as $R^4$ but is no hydrogen, in the stoichiometric ratio necessary for the formation of the formula I compound with an α,β-unsaturated nitrile of the following general formula IV:

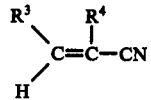  IV in which $R^3$ and $R^4$ have the meanings given above, the reaction being effected in a single stage at a temperature between 0° and 35° C in the presence of water or water-solvent mixture and a catalyst selected from the group consisting of a chloride, sulfate and acetate of cadmium, nickel, manganese and cobalt in a proportion of 0.1 to 10 millimols in admixture with ammonia or an alkali metal or alkaline earth metal hydroxide in a proportion of 0.01 to 0.2 mol based on the reactants, and separating the above formula I compounds from the reaction product.

2. The process as claimed in claim 1, wherein the catalyst is used in a proportion of 1 to 5 millimols, based on the reactants.

3. The process as claimed in claim 1, wherein the ammonia, alkali metal or alkaline earth metal hydroxide is used in a proportion of 0.05 to 0.15 mol, based on the reactants.

4. The process as claimed in claim 1, wherein the reaction is effected at a temperature between 15° and 25° C.

5. The process as claimed in claim 1, wherein the solvent is an alcohol or acetonitrile.

6. The process as claimed in claim 1, wherein the reaction is effected under nitrogen.

7. The process as claimed in claim 1, wherein the formula IV α,β-unsaturated nitrile is placed together with a catalyst in an aqueous phase consisting of water or a solvent-water mixture, the formula III compound is added at the rate necessary to maintain the reaction temperature between 15° and 25° C, the solvent is removed, and the resulting formula I tertiary phosphine oxide is separated from the reaction product.

* * * * *